United States Patent [19]

Gosser

[11] 4,302,435
[45] Nov. 24, 1981

[54] HYDROGENATION OF A DIARYLKETONE TO A DIARYLMETHANOL

[75] Inventor: Lawrence W. Gosser, Wilmington, Del.

[73] Assignee: E. I. Du Pont de Nemours and Company, Wilmington, Del.

[21] Appl. No.: 189,059

[22] Filed: Sep. 22, 1980

[51] Int. Cl.$^3$ .................. C07C 29/136; C01B 15/026
[52] U.S. Cl. ..................................... 423/591; 568/809
[58] Field of Search ........................ 568/809; 423/591

[56] References Cited

U.S. PATENT DOCUMENTS 2,871,104  1/1959  Rust ..................................... 423/591

FOREIGN PATENT DOCUMENTS 871830  7/1961  United Kingdom ................ 423/591

OTHER PUBLICATIONS

Coffey, "Rodd's Chemistry of Carbon Compounds", 1974, pp. 65, 76–79.
Blatt, "Organic Syntheses", Collective vol. I, 1948, pp. 90, 91.
Werbel et al., "J. Org. Chem.", vol. 29 (1964), pp. 967, 968.
Lindlar et al., "Organic Syntheses", Collective vol. V, 1973, pp. 880–883.
Lindlar, "Helv. Chim. Acta.", 35, (1952), pp. 446–450.
Fieser et al., "Reagents for Organic Synthesis", vol. 1, (1967), pp. 566, 567.
Strem Catalog, No. 9, 1980–1981, pp. 69, 185, 199.

Primary Examiner—Joseph E. Evans

[57] ABSTRACT

Process comprising contacting and reacting a diarylketone of the formula RCOR', wherein each of R and R' is aryl, the same or different, and hydrogen over at least a catalytic amount of lead-poisoned palladium catalyst, for example, Lindlar catalyst, at a hydrogen gage pressure in the range from about 150 kPa to about 15,000 kPa, preferably from about 340 kPa to about 3400 kPa, at a temperature in the range from about 50° C. to about 200° C., preferably from about 100° C. to about 150° C., to produce diarylmethanol of the formula RCHOHR', wherein R and R' are as defined above.

14 Claims, No Drawings

HYDROGENATION OF A DIARYLKETONE TO A DIARYLMETHANOL

DESCRIPTION

1. Technical Field

This invention relates to a process for the selective hydrogenation of a diarylketone to the corresponding diarylmethanol.

2. Background

The reduction of benzophenone to benzhydrol is well known in the art. As disclosed in "Rodd's Chemistry of Carbon Compounds", edited by S. Coffey, Elsevier Scientific Publishing Company, New York, 1974, the reduction can be carried out catalytically or chemically. A copper chromite catalyst at 175° C. and 150 atmospheres ($150 \times 10^5$ Pa) pressure is said to be effective in the hydrogenolysis of the ketone to the corresponding alcohol. The reaction can also be carried out using zinc and aqueous alkali. This method is further described by Wiselogle and Sonneborn in "Organic Syntheses", Collective Vol. I, John Wiley and Sons, Inc., New York, 1948. Alternatively, a reducing agent that is a source of hydride ion can be employed; for example, sodium hydride in xylene, diborane with pyridine in toluene and lithium tetrahydridoaluminate are effective. Still further disclosed in the art is the use of the Meerwein-Ponndorf-Verley reaction with aluminum propoxide-propanol-hydrochloric acid to convert benzophenone to benzhydrol.

A difficulty which may be encountered in connection with the use of such aforesaid processes is that competing reactions may interfere with the formation of the alcohol. For example, by-products of such aforesaid processes with benzophenone may include diphenylmethane or dibenzhydryl ether along with the desired benzhydrol.

Werbel et al, J. Org. Chem., 29,967 (1964), disclose the use of a nicotinamide-poisoned palladium on carbon catalyst in the hydrogenation of 4-methylbenzophenone to 4-methylbenzhydrol. In the absence of sufficient nicotinamide, the hydrogenation proceeds rapidly to bis(4-methylphenyl)methane.

Lindlar catalyst, lead-poisoned palladium on calcium carbonate, is well known for hydrogenating acetylenes to ethylenes, for example, phenylacetylene to phenylethylene (styrene). Such a process is described by Lindlar and Dubuis in "Organic Syntheses", Collective Vol. V, 1973, page 880. Lindlar catalyst is available commercially, with suggested uses such as the conversions of acetylenes to cis-ethylenes and cumulenes to cis-polyenes.

It is an object of the invention to provide a process which is selective for the conversion of a diarylketone to a diarylmethanol, for example, benzophenone to benzhydrol. Another object is to provide such a process which minimizes the formation of undesirable by-products such as a diarylmethane or diarylmethyl ether. Still another object is to provide a process for selectively hydrogenating a diarylketone to a diarylmethanol by means of a catalyst which not only minimizes the formation of diarylmethane and diarylmethyl ether by-products, but does so without resort to the introduction of a potentially undesirable contaminant, such as nicotinamide, which may be difficult or uneconomical to remove from the product diarylmethanol, for example, because it is soluble therewith in the system. Other objects will become apparent hereinafter.

DISCLOSURE OF INVENTION

For further comprehension of the invention, and of the objects and advantages thereof, reference may be made to the following description and to the appended claims in which the various novel features of the invention are more particularly set forth.

The invention herein resides in the discovery that lead-poisoned palladium catalyst can be used to hydrogenate selectively a diarylketone to a diarylmethanol. For example, through use of this catalyst with benzophenone, the amounts of undesirable by-products diphenylmethane and dibenzhydryl ether are minimized without resort to the use of materials, such as nicotinamide, which may result in the product containing undesirable contaminants. More specifically, the invention resides in the process wherein the diarylketone of the formula RCOR', wherein each of R and R' is aryl, the same or different, is contacted and reacted with hydrogen over at least a catalytic amount of lead-poisoned palladium catalyst, at a hydrogen gage pressure in the range from about 150 kPa to about 15,000 kPa, preferably from about 340 kPa to about 3400 kPa, at a temperature in the range from about 50° C. to about 200° C., preferably from about 100° C. to about 150° C., to produce diarylmethanol of the formula RCHOHR', wherein R and R' are as defined above. Preferably, the diarylketone has 13 to 25 carbon atoms and the most preferred diarylketone is benzophenone. An aryl group is defined herein as a monovalent radical formed conceptually by removal of a hydrogen atom from a hydrocarbon that is structurally composed entirely of one or more benzene rings. Examples of such hydrocarbons include benzene, biphenyl, terphenyl, naphthalene, phenylnapthalene, and napthylbenzene. Thus, each of R and R' can contain two fused benzene rings, one or more nonfused benzene rings, or both. It is to be understood that the R groups can be substituted, for example, with one or more substituents that are substantially inert under the reaction conditions, i.e., do not substantially adversely affect the process of the invention. Included among such substituents are alkyl, for example, methyl, and aryl, for example, phenyl (Example 5 herein).

The lead-poisoned palladium catalyst can be unsupported or supported. An example of such a supported catalyst is the well known and readily available Lindlar catalyst which is known for the hydrogenation of triple bonds to double bonds and is described by Lindlar in Helv. Chim. Acta, 35, 446 (1952) and by Lindlar et al. in "Organic Syntheses", Collective Vol. V, 1973, page 880. It comprises "conditioned" or "poisoned" palladium on calcium carbonate, the conditioning or poisoning resulting from treatment of the palladium on calcium carbonate with lead acetate. The catalyst usually contains about 5 weight percent palladium on calcium carbonate, with the weight ratio of lead to palladium being of the order of 1 to 10. It is readily available commercially.

The catalyst must be present in an amount sufficient to significantly affect the reaction. For the Lindlar catalyst, the catalyst should be at least about 1 percent by weight of the diarylketone, with preferred amounts ranging from about 5 to about 15 weight percent. Larger amounts of catalyst ranging up to 100 weight percent or more can be used.

A mixture of diarylketone and the lead-poisoned palladium catalyst is placed in a pressure vessel. In the Examples, a glass pressure bottle or an autoclave, is used. However, any conventional gas-liquid-solid reactor can be used, for example, a trickle bed reactor, bubble column, or sparged stirred tank. Optionally, the mixture can include a solvent for the diarylketone, preferably a polar solvent, for example, a butanol. The pressure vessel is evacuated and filled with hydrogen. The pressure vessel is then heated to a temperature in the range from about 50° C. to about 200° C., preferably from about 100° C. to about 150° C., and the vessel is pressured with hydrogen to reach and maintain the gage pressure in the range from about 150 kPa to about 15,000 kPa, preferably from about 340 kPa to about 3400 kPa. During the hydrogenation, the reaction mixture is agitated, for example, magnetically stirred, or shaken. Reaction times of at least 2–15 hours are generally used. Generally, reaction times vary inversely with the temperatures and pressures. After completion of the reaction, the pressure vessel is cooled to room temperature and the pressure is reduced to atmospheric pressure.

The diarylmethanol product can be separated from other components of the reaction mixture by conventional means, such as filtration and distillation.

In addition to eliminating the need to add a soluble component such as nicotinamide to the system to achieve selectivity, the lead-poisoned palladium catalyst used herein provides good selectivity at temperatures up to about 200° C. Selectivity at these higher temperatures is a particular advantage for a preferred embodiment of the process of the invention which resides in the use thereof in an integrated process for the formation of hydrogen peroxide. More specifically, it has been discovered that the diarylmethanol produced herein can be oxidized to the corresponding diarylketone with oxygen, with the concomitant production of hydrogen peroxide which can facilely be removed from the reaction mixture. The diarylketone thus produced in the oxidation reaction can then be hydrogenated to the diarylmethanol and reused in the cyclic integrated process. An embodiment of such an integrated process may be recited as follows.

In an integrated cyclic process for preparing hydrogen peroxide by oxidizing a diarylmethanol and thereafter hydrogenating the resultant diarylketone back to the diarylmethanol, the improvement characterized is that the process includes the following steps, not necessarily carried out in the order given:

(a) diarylmethanol having 13 to 25 carbon atoms and of the formula RCHOHR', wherein each of R and R' is aryl, the same or different, is contacted and reacted in the liquid state, at about 130°–260° C., with gaseous oxygen to produce hydrogen peroxide and diarylketone of the formula RCOR', wherein R and R' are as defined above; and (b) diarylketone having 13 to 25 carbon atoms and of the formula RCOR', wherein each of R and R' is aryl, the same or different, is contacted and reacted with hydrogen over at least a catalytic amount of lead-poisoned palladium catalyst at a hydrogen gage pressure in the range from about 150 kPa to about 15,000 kPa, preferably from about 340 kPa to 3400 kPa, at a temperature in the range from about 50° C. to about 200° C., preferably from about 100° C. to about 150° C., to produce diarylmethanol of the formula RCHOHR', wherein R and R' are as defined above, provided, however, the diarylmethanol and diarylketone, respectively, are the same in both steps.

EXAMPLE 1

A mixture of 2.0 g of benzophenone, 20 ml of t-butanol and 0.20 g of Lindlar catalyst (Strem Chemicals, Inc. Catalyst 46-2020; 5% palladium on calcium carbonate, lead-poisoned) was placed in a glass pressure bottle. A bottle was evacuated and then filled with hydrogen. The bottle was heated with an oil bath (115° C.) and stirred with a magnetic stirrer. Hydrogen was admitted at intervals as needed to maintain the gage pressure at about 50 psi (340 kPa). After 6 hours and 40 minutes the bottle was cooled to room temperature and the pressure was released. Catalyst was removed by filtration and the liquid was analyzed by gas chromatography with a 150"×40" (0.3×101.6 cm) stainless steel column with SP 1000 packing. Analysis indicated that diphenylmethane, benzophenone, and benzhydrol were present in the relative amounts of 0.08/47/53. The presence of diphenylmethane, benzophenone and benzhydrol was confirmed by GC-mass spectrometry. Analysis by emission spectroscopy confirmed calcium, palladium, and lead as major components of the catalyst. Wet chemical analysis showed that the catalyst contained 4.9% palladium and 0.45% lead.

EXAMPLE 2

The apparatus and reaction mixture were substantially the same as in Example 1. The oil bath temperature was 100° C., and the hydrogen gage pressure was 80 psi (550 kPa) for 15 hours. Gas chromatography analysis with a $\frac{1}{8}$"×10 ft (0.3×304.8 cm) stainless steel SP 1000-packed column indicated that the liquid in the pressure bottle contained, in the relative amounts: diphenylmethane, 0.1; benzophenone, 14; and benzhydrol, 86. The identities were confirmed by GC-mass spectrometry.

EXAMPLE 3

A mixture of 0.1 g of Lindlar catalyst and 1.0 g of benzophenone was placed in a 10 ml autoclave. The mixture was shaken for 2 hours with hydrogen at a gage pressure of 500 psi (3400 kPa) at 150° C. GC analysis with a 1 ft (30.5 cm) glass column with SP 1000 packing indicated, in the relative amounts: diphenylmethane, 0.2; benzophenone, 25; and benzhydrol, 74. The identities were confirmed by GC-mass spectrometry.

EXAMPLE 4

Commercial β-benzoylnapthalene was purified by chromatography through a silica gel column with CH2Cl2 solvent, followed by crystallization from petroleum ether to give a white powder, m.p. 81°–82° C. The apparatus of Example 1 was charged with 1.0 g of this purified β-benzoylnaphthalene, 0.1 g of Lindlar catalyst and 10.0 ml of n-butanol. The mixture was stirred under hydrogen at a gage pressure of 80 psi (550 kPa) at 127° C. for 7.5 hours. An additional 0.2 g of catalyst was added and the pressure/temperature conditions were restored and maintained for 2 hours. GC analysis with the 1 ft (30.5 cm) glass SP 1000-packed column indicated 79% of 2-naphthyl(phenyl)methanol and 21% of unreacted β-benzoylnaphthalene. No diarylmethane was detected. The GC analysis was supported by GC-mass spectrometry and nmr analyses.

EXAMPLE 5

The apparatus of Example 1 was charged with 1.0 g of commercial 4-benzoylbiphenyl, 0.10 g of Lindlar catalyst and 10.0 ml of n-butanol. The reaction time was 4 hours at 127° C. and a hydrogen gage pressure of 70 psi (480 kPa). GC analysis with the 1 ft (30.5 cm) SP 1000-packed column indicated, in the relative amounts: biphenyl, 1; 4-benzoylbiphenyl, 11; and 4-biphenylyl(phenyl)methanol, 88. The same relative amount of biphenyl was present as an impurity in the 4-benzoylbiphenyl starting material. The GC analysis was supported by GC-mass spectrometry and nmr analyses.

BEST MODE FOR CARRYING OUT THE INVENTION

The best mode for carrying out the process of the invention depends upon the economics of the particular application. Examples 1 to 3 provide representative conditions for preferred embodiments.

INDUSTRIAL APPLICABILITY

The invention provides an improved process for preparing a diarylmethanol such as benzhydrol from a diarylketone such as benzophenone, using lead-poisoned palladium catalyst, e.g., the readily available Lindlar catalyst.

Although preferred embodiments of the invention have been illustrated and described in the above disclosure, it is to be understood that there is no intent to limit the invention to the precise constructions herein disclosed, and it is to be further understood that the right is reserved to all changes and modifications coming within the scope of the invention as defined in the appended claims.

I claim:

1. Process comprising contacting and reacting a diarylketone of the formula RCOR', wherein each of R and R' is aryl, the same or different, and hydrogen over at least a catalytic amount of lead-poisoned palladium catalyst at a hydrogen gage pressure in the range from about 150 kPa to about 15,000 kPa, at a temperature in the range from about 50° C. to about 200° C., to produce diarylmethanol of the formula RCHOHR', wherein R and R' are defined as above.

2. Process of claim 1 wherein the diarylketone and diarylmethanol each have 13 to 25 carbon atoms.

3. Process of claim 2 wherein the diarylketone is benzophenone and the diarylmethanol is benzhydrol.

4. The process of claim 1 wherein the lead-poisoned palladium catalyst is Lindlar catalyst.

5. Process of claim 1 wherein the hydrogen gage pressure is in the range from about 340 kPa to about 3400 kPa, and the temperature is in the range from about 100° C. to about 150° C.

6. Process of claim 5 wherein the diarylketone and diarylmethanol each have 13 to 25 carbon atoms.

7. Process of claim 6 wherein the diarylketone is benzophenone and the diarylmethanol is benzhydrol.

8. Process of claim 5 wherein the lead-poisoned catalyst is Lindlar catalyst.

9. In an integrated cyclic process for preparing hydrogen peroxide by oxidizing a diarylmethanol and thereafter hydrogenating the resultant diarylketone back to the diarylmethanol, the improvement characterized is that the process includes the steps:

(a) diarylmethanol having 13 to 25 carbon atoms and of the formula RCHOHR', wherein each of R and R' is aryl, the same or different, is contacted and reacted, in the liquid state, at about 130°–260° C., with gaseous oxygen to produce hydrogen peroxide and diarylketone of the formula RCOR', wherein R and R' are as defined above; and (b) diarylketone having 13 to 25 carbon atoms and of the formula RCOR', wherein each of R and R' is aryl, the same or different, is contacted and reacted with hydrogen over at least a catalytic amount of lead-poisoned palladium catalyst at a hydrogen gauge pressure in the range from about 150 kPa to about 15,000 kPa, a temperature in the range from about 50° C. to about 200° C., to produce diarylmethanol of the formula RCHOHR', wherein R and R' are as defined above, provided, however, R and R', respectively, are the same in both steps.

10. Process of claim 9 wherein the diarylketone is benzophenone and the diarylmethanol is benzhydrol.

11. Process of claim 9 wherein the lead-poisioned palladium catalyst is Lindlar catalyst.

12. Process of claim 9 wherein, in step (b), the hydrogen gage pressure is in the range from about 340 kPa to about 3400 kPa, and the temperature is in the range from about 100° C. to about 150° C.

13. Process of claim 12 wherein the diarylketone is benzophenone and the diarylmethanol is benzhydrol.

14. Process of claim 12 wherein the lead-poisoned palladium catalyst is Lindlar catalyst.

* * * * *